(12) United States Patent
Zechlin et al.

(10) Patent No.: US 10,435,353 B2
(45) Date of Patent: Oct. 8, 2019

(54) METHOD FOR PRODUCING ISOCYANATES

(71) Applicant: COVESTRO DEUTSCHLAND AG, Leverkusen (DE)

(72) Inventors: Joachim Zechlin, Neuss (DE); Tim Loddenkemper, Dormagen (DE); Friedhelm Steffens, Leverkusen (DE); Dietmar Wastian, Dormagen (DE)

(73) Assignee: COVESTRO DEUTSCHLAND AG, Leverkusen (DE)

( * ) Notice: Subject to any disclaimer, the term of this patent is extended or adjusted under 35 U.S.C. 154(b) by 0 days.

(21) Appl. No.: 15/776,937

(22) PCT Filed: Nov. 29, 2016

(86) PCT No.: PCT/EP2016/079072
§ 371 (c)(1),
(2) Date: May 17, 2018

(87) PCT Pub. No.: WO2017/093215
PCT Pub. Date: Jun. 8, 2017

(65) Prior Publication Data
US 2018/0370907 A1    Dec. 27, 2018

(30) Foreign Application Priority Data
Dec. 3, 2015 (EP) ..................... 15197775

(51) Int. Cl.
C07C 263/10    (2006.01)

(52) U.S. Cl.
CPC .................. *C07C 263/10* (2013.01)

(58) Field of Classification Search
CPC ..................................... C07C 263/10
USPC ........................................... 560/347
See application file for complete search history.

(56) References Cited

U.S. PATENT DOCUMENTS

| | | | |
|---|---|---|---|
| 4,847,408 A | 7/1989 | Frosch et al. | |
| 6,706,913 B2 | 3/2004 | Leimkühler et al. | |
| 6,838,578 B2 | 1/2005 | Leimkühler et al. | |
| 6,930,199 B2 | 8/2005 | Meyn et al. | |
| 6,974,880 B2 | 12/2005 | Biskup et al. | |
| 7,019,164 B2 | 3/2006 | Friedrich et al. | |
| 8,258,337 B2 | 9/2012 | Woelfert et al. | |
| 8,692,016 B2 | 4/2014 | Sanders et al. | |
| 8,957,245 B2 | 2/2015 | Olbert et al. | |
| 2010/0210870 A1* | 8/2010 | Olbert .............. | C07C 263/10 560/347 |
| 2017/0283370 A1 | 10/2017 | Sanders et al. | |

* cited by examiner

*Primary Examiner* — Deborah D Carr
(74) *Attorney, Agent, or Firm* — Donald R. Palladino

(57) ABSTRACT

The invention relates to the production of isocyanates by means of phosgenation of the corresponding primary amines in the gas phase, wherein the reactant flows of amine and phosgene are fed separately to a reactor through a pre-heated inert gas flow. Isocyanates within the sense of the invention are, in the broadest sense, all isocyanates whose corresponding amines can be substantially converted into the gas phase without decomposing, with the exception of 1,5-pentane diisocyanate.

16 Claims, 1 Drawing Sheet

METHOD FOR PRODUCING ISOCYANATES

CROSS-REFERENCE TO RELATED APPLICATIONS

This application is a national stage application under 35 U.S.C. § 371 of PCT/EP2016/079072, filed Nov. 29, 2016, which claims the benefit of European Application No. 15197775.8, filed Dec. 3, 2015, both of which are being incorporated by reference herein.

FIELD

The present invention is concerned with the preparation of isocyanates by phosgenating the corresponding primary amines in the gas phase, wherein the amine and phosgene reactant streams are fed to a reactor separately by a preheated inert gas stream. Isocyanates in the context of the invention are, in the broadest sense, all isocyanates whose corresponding amines can be converted to the gas phase essentially without decomposition, except for pentane 1,5-diisocyanate.

BACKGROUND

Isocyanates are prepared in large volumes and serve mainly as starting materials for preparation of polyurethanes.

The production of isocyanates in the gas phase is associated with the formation of specific by-products that are solid or dissolved under the reaction conditions, for example isocyanurates, biurets, allophanates, carbodiimides or ureas.

Although these solid by-products—depending on the reaction conditions—form in low concentrations, they can lead to unpleasant deposition problems in specific process sections.

In the production of isocyanates in the gas phase, it has been found to be useful to contact the amine and phosgene reactants with one another by means of static mixing units, especially by means of nozzles. This can be accomplished, for example, by "jetting" the amine through a nozzle into a phosgene stream surrounding the nozzle. The inverse procedure (jetting phosgene into an amine stream surrounding the nozzle) is also conceivable, as is the use of two-phase nozzles for amine and phosgene. In each case, the problem arises that the gaseous amine and phosgene reactants come into contact with one another directly at the exit orifice of the nozzle. For this reason, the formation of the solid by-products begins there as well and can lead to deposits at the exit orifice of the nozzle.

These deposits at the exit orifice of the nozzle, under the conditions of the gas phase process, lead to additional vortexing and hence uneven radial distribution of the amine in the phosgene. These additional vortexes allow the reaction mixture to come into contact with the reactor wall at the early stage of the entry region of the reactor—with formation of solid deposits on the reactor wall. As a result, the free cross section of the reactor decreases ever further at the early stage of the entry region, with formation of an elevated pressure differential, which ultimately entails a premature shutdown for cleaning.

In the case of deposits at the exit orifice of the nozzle, in addition to the aspect of the shortening of the reactor service life, a worsened spectrum of by-products is observed since the additional vortexing at the exit orifice of the nozzle results in uncontrolled backmixing of reaction mixture. This gives rise to a dwell time profile in the reactor which is no longer exactly defined, and this has an unfavorable effect on the formation of by-products.

It is therefore desirable that, in the case of preparation of isocyanates in the gas phase, the phosgene and amine reactants do not come into contact with one another immediately at the exit orifice of the nozzle, but only at a certain distance therefrom.

Such a process variation would reduce the occurrence and hence also the deposition of solid by-products at the nozzle. In addition, such a process variation would homogenize the dwell time spectrum, which leads to a reduction in by-product formation.

WO 2009/027232 A1 details a method of metering an inert gas into a gap between the amine stream and the phosgene stream. It is stated therein that this additional metering of inert gas delays the main portion of the mixing of amine stream and phosgene stream in order to avoid the formation of solids at the nozzle tip.

However, a disadvantage of this method is that the inert gas added inevitably brings about cooling of the nozzle unless it—like the amine stream itself—is sufficiently overheated. However, no such overheating is disclosed in WO 2009/027232 A1.

The unpublished international patent application PCT/EP2015/071438 is concerned exclusively with a process for preparing pentane 1,5-diisocyanate (PDI).

In the case of inert gas-induced cooling of the nozzle, partial condensation of amine on the inner wall of the nozzle is likely. This is especially true in the case of an already elevated pressure differential through the reactor, which after a prolonged reactor run time already results in an elevated condensation temperature for the amine. Partially condensing amine would be discharged from the nozzle as droplets which in turn form deposits at the nozzle mouth after a certain time—as a result of thermal stress alone or else as a result of incomplete reaction with phosgene which is also present at the nozzle mouth in low concentrations.

There was therefore still a need for a simple and inexpensive modification of the process for preparing isocyanates in the gas phase with a sufficiently reduced tendency to deposition of solids at the nozzle, which avoids the specific disadvantages of the prior art processes.

SUMMARY

It has now been found that, surprisingly, the tendency to deposition of solid by-products at the nozzle can be drastically reduced when the amine is reacted with phosgene in the gas phase under specific conditions—which are especially characterized in that the gaseous inert substance stream is heated to a temperature of 100° C. to 500° C., preferably 150° C. to 450° C., more preferably 150° C. to 400° C.—as described hereinafter. At the same time, it was also shown that, surprisingly, the yield of the process on employment of the conditions described hereinafter is higher than on employment of the conditions that are described in the prior art.

The present invention provides a process for continuously preparing an isocyanate (4) other than pentane 1,5-diisocyanate, by reacting the corresponding primary amine (1) with phosgene (2) in the presence of an inert substance (3), comprising the following steps:

(i) providing a gas stream (10) comprising the primary amine at a temperature of 200° C. to 430° C., preferably 250° C. to 420° C., more preferably 250° C. to 400° C.;

(ii) providing a phosgene-containing gas stream (20) at a temperature of 200° C. to 430° C., preferably 250° C. to 420° C., more preferably 250° C. to 400° C.;
(iii) providing a gaseous inert substance stream (30) at a temperature of 100° C. to 500° C., preferably 150° C. to 450° C., more preferably 150° C. to 400° C.;
(iv) feeding the streams 10, 20 and 30 from steps (i) to (iii) into a reactor (2000) for reaction of the primary amine (1) with the phosgene (2) in the gas phase, wherein
  a) the reactor (2000) has flow connection to an at least twin-wall tube (1000—also referred to as "annular gap nozzle or separation gap nozzle") comprising a first wall (1200) that encloses the inner portion (1100) of the tube and a second wall (1400) that forms a gap (1300) with the outside of the first wall;
  b) either the stream 10 or the stream 20, preferably stream 10, is guided through the inner portion (1100) of the at least twin-wall tube into the reactor;
  c) the stream 30 is guided through the gap 1300 between the first wall and the second wall of the at least twin-wall tube into the reactor;
  d) that stream 10 or 20 which is not guided through the inner portion of the twin-wall tube, i.e. preferably stream 20, is guided past the outside of the second wall (1400) of the at least twin-wall tube such that it comes into contact with the stream 30 at the end of the at least twin-wall tube;
(v) working up the gaseous crude product stream (40) formed in the reactor (2000) to obtain the desired isocyanate (4).

DETAILED DESCRIPTION

Figure 1:
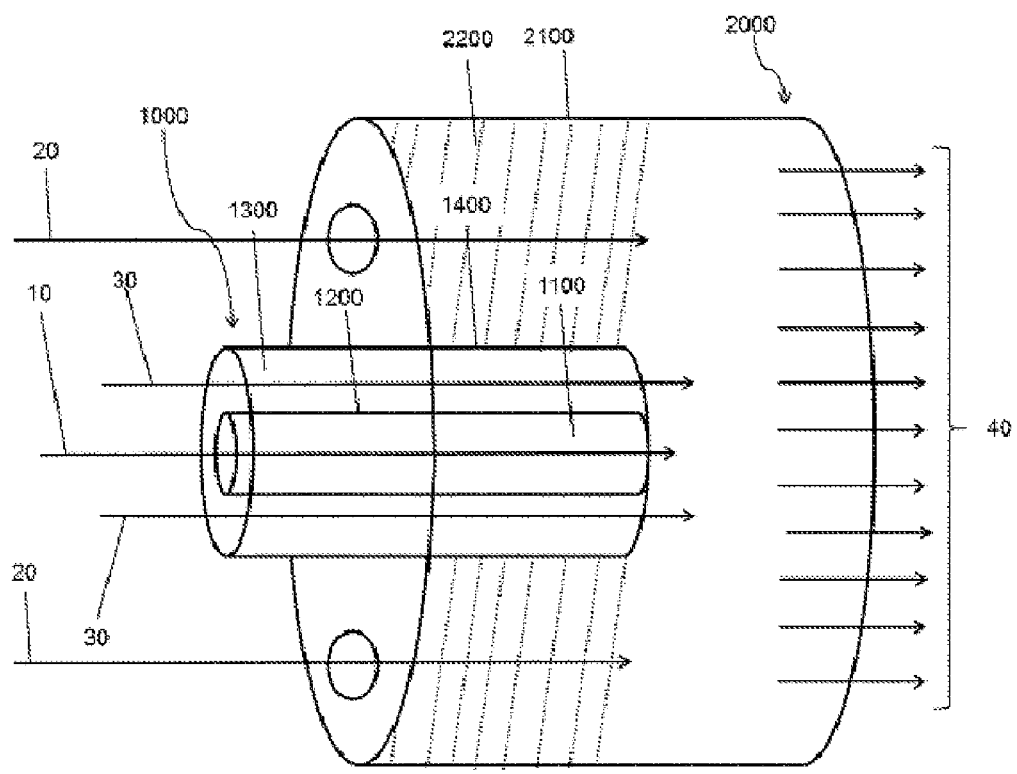
FIG. 1 illustrates a twin-wall tube projecting into the interior of a reactor such that the inside of the wall of the reactor and the outside of the second wall of the tube form a gap through which stream 10 or 20 is guided, according to an embodiment of the invention.

The invention is suitable for preparing all isocyanates whose corresponding amines can be converted to the gas phase essentially without decomposition. However, the invention does not cover the preparation of pentane 1,5-diisocyanate. More particularly, the isocyanate (4) may be selected from (I) the group consisting of xylylene diisocyanate, hexamethylene diisocyanate, isophorone diisocyanate, phenyl isocyanate, methylene diphenylmethane diisocyanate and tolylene diisocyanate. More preferably, the isocyanate (4) is selected from (II) the group consisting of xylylene diisocyanate, hexamethylene diisocyanate and tolylene diisocyanate. Most preferably, the isocyanate (4) is selected from (III) the group consisting of tolylene diisocyanate and hexamethylene diisocyanate. Very exceptionally preferred is (IV) the preparation of tolylene diisocyanate (TDI henceforth, 4a) by phosgenation of tolylenediamine (TDA henceforth, 1a). The above-described groups (I), (II), (III) and (IV) of preferred isocyanates (4) should each be regarded as conclusive lists, meaning that, in the particular preferred embodiment, the isocyanate (4) is selected exclusively from the members of the respective group.

There follows a description of embodiments of the invention. Various embodiments may be combined with one another as desired, unless the opposite is apparent to the person skilled in the art from context.

The phosgenation of amines in the gas phase per se is known and can be effected as described, for example, in EP 0 289 840 B1, EP 1 319 655 A2, EP 1 555 258 A1, EP 1 275 639 A1, EP 1 275 640 A1, EP 1 449 826 A1, EP 1 754 698 B1, DE 10 359 627 A1 or in German patent application DE 10 2005 042392 A1.

In the preferred embodiment of the phosgenation of TDA (1a), preferably, TDA having a purity of >99.5% determined by gas chromatography and a water content of <300 ppm determined by Karl Fischer titration. The preparation of TDA is known from the prior art. It is immaterial to the invention whether the TDA comes from petrochemical-based or "bio-based" raw materials. This of course also applies to other primary amines (1).

Prior to the performance of the process of the invention, the primary amine (1) is evaporated and heated to a temperature of 200° C. to 430° C., preferably of 250° C. to 420° C., more preferably of 250° C. to 400° C., and fed to the reactor (2000) which is preferably configured as a tubular reactor. The primary amine here is preferably admixed with an inert substance (3) such as nitrogen, He, Ar or the vapors of an inert solvent, for example an aromatic hydrocarbon with or without halogen substitution, for example chlorobenzene, ortho-dichlorobenzene, toluene, chlorotoluene, xylene, chloronaphthalene or decahydronaphthalene, preferably chlorobenzene or ortho-dichlorobenzene, especially preferably ortho-dichlorobenzene. The gaseous stream of amine and any gaseous admixtures present is referred to as gas stream 10. The abovementioned temperatures, in the case that admixtures are present, are applicable to the entire stream 10.

The phosgene (2) used in the phosgenation, before being fed into the reactor (2000), is likewise heated to a temperature of 200° C. to 430° C., preferably of 250° C. to 420° C., more preferably of 250° C. to 400° C. The abovementioned inert substances may also be mixed into the phosgene. The stream of gaseous phosgene and any gaseous admixtures present is referred to gas stream 20. The abovementioned temperatures, in the case that admixtures are present, are applicable to the entire stream 20.

It is essential to the invention that the amine stream 10 and phosgene stream 20 are fed to the reactor in such a way that they do not come into contact with one another immediately after exit from the respective feed tube. It is likewise essential to the invention that this avoidance of immediate contact is effected such that there is no unwanted cooling of the reactants in the separated and/or mixed state. For this purpose, it is essential to provide an inert gas stream (30) comprising the same inert substances as are suitable for the dilution of the amine stream and/or the phosgene stream and have been described above. This inert gas stream is thus heated in accordance with the invention to a temperature of 100° C. to 500° C., preferably 150° C. to 450° C., more preferably 150° C. to 400° C., and fed to the reactor as described hereinafter.

In a preferred embodiment, the tube (1000) has exactly two walls (1200, 1400) and projects into the interior of the reactor such that the inside of the wall (2100) of the reactor (2000) and the outside of the second wall (1400) of the tube form a gap (2200) through which the stream 10 or 20 is guided in step (iv) d). In this embodiment, the inner reactor wall together with the outside of the second wall thus (1400) forms the second boundary of the stream according to (iv)

d). This embodiment is shown in FIG. 1. The separate preheating of the additionally metered inert gas stream (30) in accordance with the invention leads to the desired avoidance of heat losses, especially in the inner portion (1100) of the at least twin-wall tube (1000). In the preferred embodiment shown in FIG. 1, in which the amine gas stream (10) is guided through the inner portion (1100) of the device 1000, the amine gas stream (10) is encased by the inert gas stream (30) in the form of a cylindrical shell. By contrast with the prior art, this enables adiabatic feeding (in other words, in this context, without significant heat losses) of the amine gas stream (10) to the reactor (2000). The adiabatic amine feed suppresses the condensation of amine on the inner wall of the inner portion (1100), as a result of which deposits at the exit orifice of the inner portion (1100) are reliably avoided. The feeding of the amine gas stream (10) through the inner portion 1100, which is shown in FIG. 1, and the feeding of the phosgene gas stream (20) through the gap 2200 is preferred for the reasons mentioned but is not obligatory, and so can also be switched. The arrangement shown in FIG. 1, in which the two walls (1200, 1400) of the twin-wall tube (1000) are of the same length, is not obligatory but is preferred. The walls (1200, 1400) may also be of different length, in which case it is preferable that the inner wall (1200) is longer than the outer wall (1400).

Figure 2:
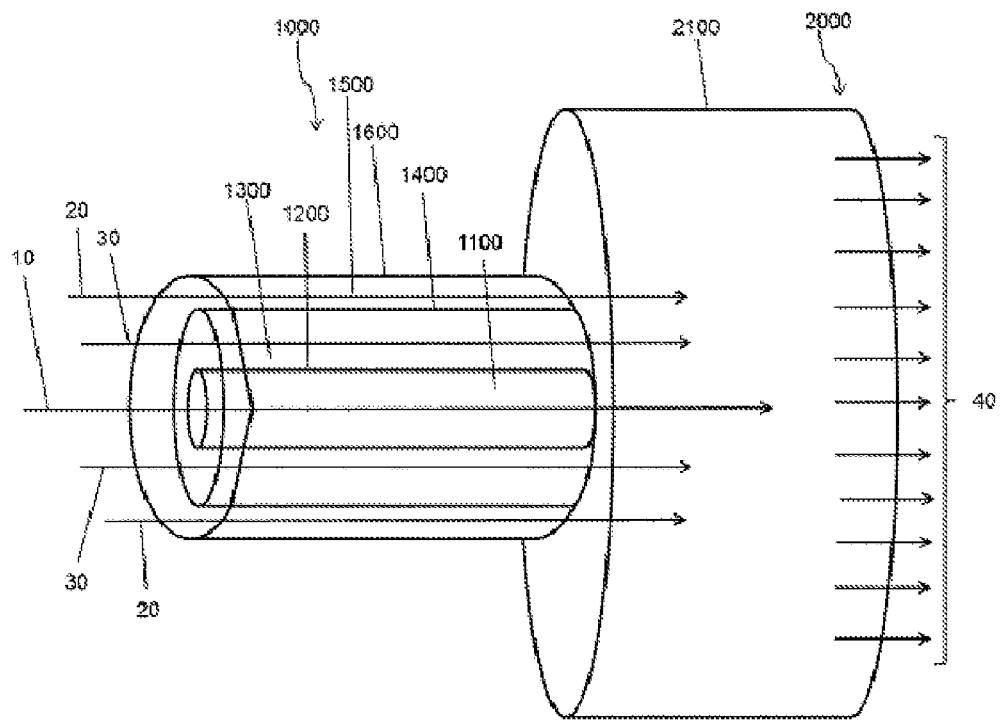
FIG. 2 illustrates a tube comprising a third wall the inside of which together with the outside of the second wall forms a gap through which the stream 10 or 20 is guided, according to an embodiment of the invention.

In another preferred embodiment, the tube (1000) additionally comprises a third wall (1600), the inside of which together with the outside of the second wall (1400) forms a gap (1500) through which the stream 10 or 20 is guided in step (iv) d). This embodiment is shown in FIG. 2. The feeding of the amine gas stream (10) through the innermost tube, which is shown therein, and the feeding of the phosgene gas stream (20) through the gap 1500 is preferred but is not obligatory, and so can also be switched. Since, in this embodiment, the outer annular gap (1500), by contrast with the above-described embodiment, is not bounded on the outside by the inner reactor wall, it is possible to flange the tube (1000) directly to the entry orifice of the reactor (2000). It is alternatively possible in this embodiment to allow the tube (1000) to project into the reactor (2000). In this embodiment too, it is preferable (but not obligatory) to guide the amine gas stream (10) through the inner portion (1100), as described above for the embodiment according to FIG. 1. The arrangement shown in FIG. 2, in which the three walls (1200, 1400, 1600) of the tube (1000) are of equal length, is not obligatory but is preferred. The walls (1200, 1400, 1600) may also be of different length, in which case it is preferable that the inner wall (1200) is longer than the outer walls (1400, 1600).

Irrespective of the exact manner in which the outer annular gap is implemented, it is preferable that the reactor (2000) has a cylindrical or conical shape (tubular reactor), the at least twin-wall tube (1000) being aligned centrally in the direction of the axis of rotation of the reactor (2000). Preferably, in the process of the invention, tubular reactors having no internals and having no moving parts within the reactor (2000) are used. The tubular reactors generally consist of steel, glass or alloyed or enameled steel, and their dimensions are such that complete reaction of the primary amine (1) with the phosgene is enabled under the process conditions. The gas streams, as described above, are introduced into the tubular reactor via an at least twin-wall tube (1000) at one end thereof. In the mixing zone downstream of the at least twin-wall tube (1000), preferably, a temperature in the range from 300° C. to 480° C., preferably 350° C. to 450° C., is sustained, and this temperature can optionally be maintained by heating the tubular reactor over its entire length.

In all embodiments, it is preferable to feed the preheated gaseous amine stream (10) that has optionally been diluted by an inert substance at a mean flow rate of 10 m/s to 150 m/s, preferably 10 m/s to 100 m/s, to the reactor (2000) according to (iv) b) or (iv) d), preferably according to (iv) b). It is likewise preferable in all embodiments to feed the preheated gaseous phosgene (20) that has optionally been diluted by an inert substance to the reactor (2000) at a mean flow rate of at least 1 m/s, preferably of 5 m/s to 15 m/s.

In all embodiments, the inert substance (3) is preferably selected from the group consisting of nitrogen, noble gases, inert solvents and mixtures of the aforementioned substances. Suitable solvents are, for example, aromatic hydrocarbons with or without halogen substitution, for example chlorobenzene, ortho-dichlorobenzene, toluene, chlorotoluene, xylene, chloronaphthalene or decahydrodronaphthalene. Preference is given to chlorobenzene and ortho-dichlorobenzene; ortho-dichlorobenzene is especially preferred. If amine (1) and/or phosgene (2) are diluted with an inert substance, preference is given to using the same inert substance (3) for this purpose, which is guided through the gap 1300 in preheated and gaseous form as stream 30. The gaseous inert substance stream (30) is preferably fed to the reactor (2000) at a mean flow rate of 10 m/s to 150 m/s, preferably of 10 m/s to 100 m/s.

The separate heating of the inert gas stream, in a particular embodiment of the present invention, permits a reaction regime in which the temperature of the gaseous phosgene-containing stream (20) provided in step (ii) is adjusted to a value below the boiling point of the primary aromatic amine (1) to be phosgenated under the conditions in step (iv), and especially up to 80° C. below the boiling point. This is especially applicable to the preferred embodiment in which the amine gas stream (10) is guided through the inner portion (1100) of the at least twin-wall tube (1000). In such a case, by virtue of the sheathing of the inner portion (1100) with the hot inert gas, there is no risk of condensation of amine (1) on the inside of the wall 1200. In this embodiment, the droplets of fine condensate that often arise in the mixing of amine gas stream (10) and phosgene gas stream (20), by virtue of the heat of reaction that arises, evaporate quickly enough to enable complete reaction within the dwell time resulting from the reactor geometry.

The advantage in the case of such an alternative reaction regime is that less heat has to be introduced into the reactor (2000). The hotspot temperature lowered as a result has a positive effect on the yield. Moreover, less energy has to be expended for the phosgene overheating and for the cooling on completion of reaction.

The flow rates of streams 10 and 20 guided into the reactor (2000) are preferably chosen such that the molar excess of phosgene over primary amino groups is 30% to 350%, preferably 60% to 250%.

Preferably, the streams 10, 20 and 30 provided in steps (i), (ii) and (iii) are each independently fed to the reactor (2000) in step (iv) under an (absolute) pressure of 400 mbar to 3000 mbar, preferably of 400 mbar to 2000 mbar, more preferably of 800 mbar to 1800 mbar. Preferably, the (absolute) pressure of the reaction mixture at the exit orifice of the reactor (2000) is in the range from 400 mbar to 2000 mbar, preferably 750 mbar to 1500 mbar, and a total flow rate within the reactor (2000) of 2.0 m/s to 100 m/s, preferably 5.0 m/s to 50 m/s, is observed by maintaining a suitable pressure differential.

With these prerequisites, there is generally plug flow within the reactor (2000), which assures a homogeneous dwell time of the reaction mixture in the reactor. The dwell time is 1.0 s to 10 s, preferably 2.0 s to 7.0 s. The dwell time is calculated from the throughput of the reactant streams against time, the reactor dimensions and the reaction parameters of pressure and temperature.

On completion of the phosgenation reaction in the reactor (2000), the gaseous mixture that leaves the reactor continuously is freed of hydrogen chloride gas and excess phosgene, and the isocyanate (4) formed is isolated. For this purpose, preferably, the gaseous crude product stream (40) obtained in the reactor (2000) is firstly cooled in step (v) by contact with an inert liquid (50), so as to obtain a liquid stream (41) comprising the desired isocyanate (4) and a gaseous stream (60) comprising hydrogen chloride and unconverted phosgene. The temperature of the inert liquid (50) here is preferably chosen such that it is on the one hand above the decomposition temperature of the carbamoyl chloride corresponding to the isocyanate (4) and on the other hand below the condensation temperature of the isocyanate (4) and preferably also of any solvent used as diluent in vapor form, such that isocyanate (4) and auxiliary solvent condense, while excess phosgene, hydrogen chloride and any inert gas used as diluent pass through the condensation stage in gaseous form. Preference is given to using the inert liquid (50) at a temperature of 100° C. to 250° C., preferably 120° C. to 190° C. The inert liquid (50) used is preferably chlorobenzene, ortho-dichlorobenzene, toluene, chlorotoluene, xylene, chloronaphthalene or decahydrodronaphthalene, more preferably chlorobenzene or ortho-dichlorobenzene, most preferably ortho-dichlorobenzene. If the inert gas stream (30) consists of the vapors of one of the aforementioned inert solvents, the inert liquid (50) used is appropriately and preferably the same solvent in liquid form.

Conceivable methods for the selective condensation of the isocyanate (4) formed out of the gas mixture (41) that leaves the reactor (2000) are, for example, the passing of the gas mixture through the inert liquid (50) or the jetting of the inert liquid (50) (solvent mist) into the gas stream 41 (called a "quench").

The gas mixture (60) which passes through the condensation stage for obtaining the isocyanate (4) and is preferably under an (absolute) pressure of 400 mbar to 2000 mbar is subsequently freed of excess phosgene in a manner known per se (phosgene recovery).

This can be effected by means of a cold trap, absorption in an inert solvent kept at a temperature of −10° C. to 8° C. (preferably the same solvent as the inert liquid 50), or by adsorption and hydrolysis on activated carbon.

The hydrogen chloride gas that passes through the phosgene recovery stage can be recycled in a manner known per se for recovery of the chlorine required for phosgene synthesis.

The preparation of the pure isocyanate (4) is preferably effected by distillative workup of the liquid, solvent-containing stream 41.

The advantages of the process of the invention are:

a) avoidance of solid deposits in the amine feed (i.e. preferably on the inside of the wall 1200) and on the inner wall of the reactor (2000) and hence an increase in the reactor service life.

b) low by-product formation and hence lower production of isocyanate residue, which distinctly reduces the amounts of waste to be utilized.

The example which follows illustrates the invention using the example of the phosgenation of TDA (1a) to TDI (4a).

EXAMPLES

Example 1 (Inventive—See FIG. 1)

In a gas phase reactor (2000), 8.8 kg/h of gaseous TDA (10; 380° C., 1600 mbar) and 42.8 kg/h of gaseous phosgene (20; 310° C., 1600 mbar) were mixed and reacted by means of an annular gap nozzle (1000). According to the invention, 0.587 kg/h of nitrogen (30) was preheated to 240° C. and metered into the gap (1300) between amine feed and phosgene feed. After a run time of 92 hours, the metering of reactants was stopped and the reactor was cooled down. Inspection of the deinstalled annular gap nozzle (1000) showed that it was virtually free of solid residues.

The invention claimed is:

1. A process for continuously preparing an isocyanate (4) other than pentane 1,5-diisocyanate, by reacting the corresponding primary amine (1) with phosgene (2) in the presence of an inert substance (3), comprising:
   (i) providing a gas stream (10) comprising the primary amine at a temperature of 200° C. to 430° C.;
   (ii) providing a phosgene-containing gas stream (20) at a temperature of 200° C. to 430° C.;
   (iii) providing a gaseous inert substance stream (30) at a temperature of 100° C. to 500° C.;
   (iv) feeding the streams (10), (20) and (30) from steps (i) to (iii) into a reactor (2000) for reaction of the primary amine (1) with the phosgene (2) in the gas phase, wherein
   a) the reactor (2000) has flow connection to an at least twin-wall tube (1000) comprising a first wall (1200) that encloses the inner portion (1100) of the tube and a second wall (1400) that forms a gap (1300) with the outside of the first wall;
   b) either the stream (10) or the stream (20) is guided through the inner portion (1100) of the at least twin-wall tube into the reactor;
   c) the stream (30) is guided through the gap (1300) between the first wall and the second wall of the at least twin-wall tube into the reactor;
   d) that stream (10) or (20) which is not guided through the inner portion of the twin-wall tube is guided past the outside of the second wall (1400) of the at least twin-wall tube such that it comes into contact with the stream (30) at the end of the at least twin-wall tube;
   (v) working up the gaseous crude product stream (40) formed in the reactor (2000) to obtain the desired isocyanate (4).

2. The process as claimed in claim 1, in which the isocyanate (4) is selected from the group consisting of xylylene diisocyanate, hexamethylene diisocyanate, isophorone diisocyanate, phenyl isocyanate, methylene diphenylmethane diisocyanate and tolylene diisocyanate.

3. The process as claimed in claim 1, in which the tube (1000) has exactly two walls (1200, 1400) and projects into the reactor such that the inside of the wall (2100) of the reactor (2000) and the outside of the second wall (1400) of the tube form a gap (2200) through which the stream (10) or (20) is guided in step (iv) d).

4. The process as claimed in claim 1, in which the tube (1000) additionally comprises a third wall (1600), the inside of which forms, with the outside of the second wall (1400), a gap (1500) through which the stream (10) or (20) is guided in step (iv) d).

5. The process as claimed in claim 4, in which the tube (1000) is flanged on to the entry orifice of the reactor (2000).

6. The process as claimed in claim 4, in which the tube (1000) projects into the reactor (2000).

7. The process as claimed in claim 3, in which the reactor (2000) has a cylindrical or conical shape and the tube (1000) is aligned centrally in the direction of the axis of rotation of the reactor (2000).

8. The process as claimed in claim 1, in which the stream (10) is guided through the inner portion (1100) of the at least twin-wall tube (1000) into the reactor (2000).

9. The process as claimed in claim 1, in which the inert substance (3) is selected from the group consisting of nitrogen, noble gases, inert solvents and mixtures thereof.

10. The process as claimed in claim 1, in which the isocyanate is tolylene diisocyanate and the tolylenediamine used as primary amine has a purity determined by gas chromatography of >99.5% and a water content determined by Karl Fischer titration of <300 ppm.

11. The process as claimed in claim 1, in which the flow rates of the streams (10) and (20) guided into the reactor are chosen such that the molar excess of phosgene over primary amino groups is 30% to 350%.

12. The process as claimed in claim 1, in which the streams (10), (20) and (30) provided in steps (i), (ii) and (iii) are each independently fed to the reactor in step (iv) under a pressure of 400 mbar to 3000 mbar.

13. The process as claimed in claim 1, in which the gaseous crude product stream (40) obtained in the reactor (2000) in step (v) is cooled down by contact with an inert liquid (50) to obtain a liquid stream (41) comprising the desired isocyanate (4) and a gaseous stream (60) comprising hydrogen chloride and unconverted phosgene.

14. The process as claimed in claim 13, in which the gaseous stream (60) comprising hydrogen chloride and unconverted phosgene is under a pressure of 400 mbar to 2000 mbar.

15. The process as claimed in claim 1, in which the temperature of the gaseous phosgene-containing stream (20) provided in step (ii) is adjusted to a value below the boiling point of the primary aromatic amine (1) to be phosgenated under the conditions in step (iv).

16. The process of claim 15, in which the temperature of the gaseous phosgene-containing stream (20) provided in step (ii) is adjusted to a value up to 80° C. below the boiling point of the primary aromatic amine (1) to be phosgenated under the conditions in step (iv).

* * * * *